(12) United States Patent
Wilson et al.

(10) Patent No.: US 9,001,187 B2
(45) Date of Patent: Apr. 7, 2015

(54) CAPSULE IMAGING SYSTEM HAVING A FOLDED OPTICAL AXIS

(75) Inventors: Gordon Cook Wilson, San Francisco, CA (US); Mark Wang, San Ramon, CA (US)

(73) Assignee: CapsoVision, Inc., Saratoga, CA (US)

( * ) Notice: Subject to any disclaimer, the term of this patent is extended or adjusted under 35 U.S.C. 154(b) by 502 days.

(21) Appl. No.: 12/877,220

(22) Filed: Sep. 8, 2010

(65) Prior Publication Data

US 2011/0001789 A1    Jan. 6, 2011

Related U.S. Application Data

(63) Continuation-in-part of application No. 12/463,488, filed on May 11, 2009.

(51) Int. Cl.
| A62B 1/04 | (2006.01) |
| H04N 7/00 | (2011.01) |
| G02B 13/06 | (2006.01) |
| A61B 1/04 | (2006.01) |
| H04N 5/225 | (2006.01) |
| H04N 5/232 | (2006.01) |
| H04N 5/341 | (2011.01) |
| G02B 17/08 | (2006.01) |

(52) U.S. Cl.
CPC ............... *G02B 13/06* (2013.01); *A61B 1/041* (2013.01); *H04N 5/2254* (2013.01); *H04N 5/23238* (2013.01); *H04N 5/3415* (2013.01); *G02B 17/08* (2013.01)

(58) Field of Classification Search
CPC ............................... A61B 1/041; G03B 17/17
See application file for complete search history.

(56) References Cited

U.S. PATENT DOCUMENTS

| 4,787,725 | A | * | 11/1988 | Preussner et al. | 359/401 |
| 5,920,337 | A | * | 7/1999 | Glassman et al. | 348/36 |
| 6,266,197 | B1 | * | 7/2001 | Glenn et al. | 359/819 |
| 6,731,845 | B1 | * | 5/2004 | Gerdt | 385/116 |
| 2003/0107789 | A1 | * | 6/2003 | Hishioka | 359/223 |
| 2004/0027451 | A1 | * | 2/2004 | Baker | 348/46 |
| 2006/0178830 | A1 | * | 8/2006 | Sherony | 701/301 |

OTHER PUBLICATIONS

File History—U.S. Appl. No. 12/463,488.

* cited by examiner

*Primary Examiner* — Joseph Ustaris
*Assistant Examiner* — Mikhail Itskovich
(74) *Attorney, Agent, or Firm* — Brosemer, Kolefas & Associates

(57) ABSTRACT

An optical imaging system having a folded optical axis.

23 Claims, 16 Drawing Sheets

CAPSULE IMAGING SYSTEM HAVING A FOLDED OPTICAL AXIS

RELATED APPLICATION

This application is a continuation-in-part of U.S. patent application Ser. No. 12/463,488 filed May 11, 2009 which in turn claimed the benefit of U.S. Provisional Application No. 61/052,180 filed May 10, 2008, both of which are incorporated by reference for all purposes into this application.

FIELD OF THE DISCLOSURE

This disclosure relates generally to the field of optical imaging and in particular to an apparatus that provides a large, wide-angle field of view with a folded image.

BACKGROUND OF THE DISCLOSURE

In a number of applications the ability to produce a large, wide-angle field of view from an imager employing a folded optical axis and a lens element before the fold is useful. Such arrangements however, have proved elusive.

SUMMARY OF THE DISCLOSURE

We have developed, in accordance with the principles of the disclosure, a folded imaging system which produces a large field of view from a folded image. Advantageously, imaging systems according to the present invention are manufacturable.

BRIEF DESCRIPTION OF THE DRAWING

A more complete understanding of the present invention may be realized by reference to the accompanying drawing in which.

DETAILED DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the disclosure.

One aspect of the present disclosure is that of a folded imaging system which exhibits a relatively large field of view (FOV) while using only a single lens element between an object and the fold. As such, a system exhibiting this aspect of the present disclosure will be sufficiently compact for an array of applications including medical imaging.

Figure 1:
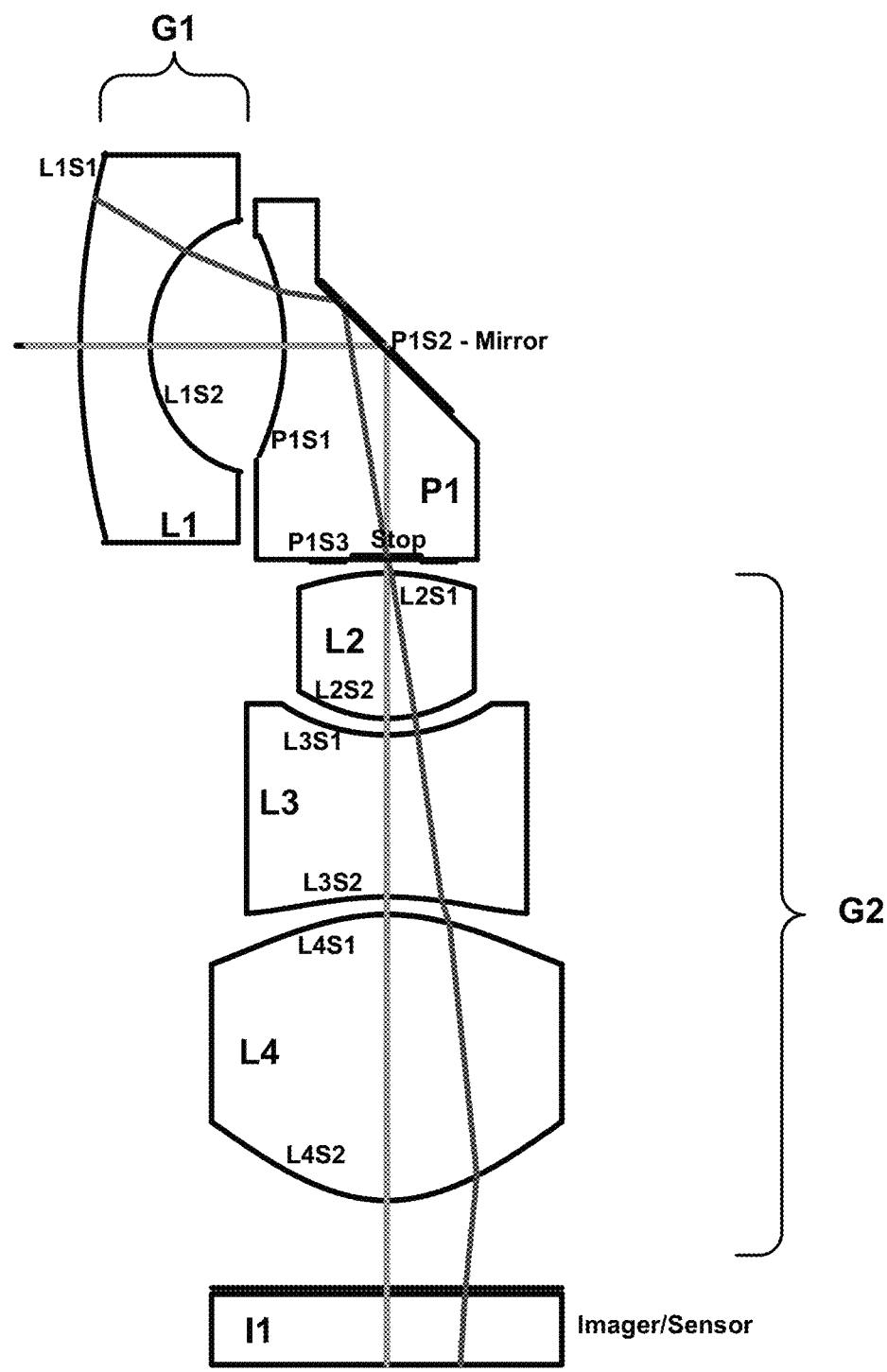
FIG. 1 shows a schematic of an exemplary folded imager according to an aspect of the present disclosure.

With reference to FIG. 1, there is shown an exemplary imaging system having a folded optical axis according to an aspect of this disclosure. As shown in that FIG. 1, an imaging system according to an aspect of the present disclosure has at least, in order from an object side, a first lens group G1 having a negative refractive power, a prism P1 having a first surface that is concave P1S1 and a second surface that is reflective (mirror) P1S2, and a second lens group G2 having a positive refractive power. An image sensor is positioned after the second lens group G2. Accordingly, light reflected from the object is imaged upon the image sensor through the effect of the first lens group G1, the prism P1, and the second lens group G2.

As may be appreciated, the mirror may be achieved by applying a reflective metallic or dielectric coating to the face of the prism. Alternatively, if the refractive index of the prism P1 is large enough to ensure total internal reflection for all field angles, then no reflective coating is required. With respect to the image sensor, it may be of any of a variety known in the art, i.e., electronic or photochemical.

As shown in FIG. 1, first lens group G1 comprises a single lens L1 having two refractive surfaces, convex surface L1S1 and concave surface L2S2, which exhibits an overall negative refractive power. The second lens group G2 is shown comprising three lenses, namely, L2, L3, and L4. Each of the lenses includes two refractive surfaces. The first lens in group G2, lens L2, has two convex refractive surfaces L2S1 and L2S2. The second lens in group G2, lens L3, has two concave refractive surfaces L3S1 and L3S2. The third lens in group G2, lens L4, has two convex refractive surfaces L4S1 and L4S2.

Interposed between the two lens groups G1 and G2 is prism P1 which produces a fold of substantially 90 degrees to the overall optical path. As depicted in FIG. 1, prism P1 has three optical surfaces. A first surface, P1S1, is a concave refractive surface. The second surface of prism P1, is a reflective surface P1S1 and finally, the third surface P2S3 is shown as being substantially flat.

In an alternative embodiment, a stop, or aperture may be positioned at this P1S3 surface. In a preferred embodiment, the chief rays will cross one another at that P1S3 surface.

Advantageously, a wide array of optical materials may be employed to construct the various elements of the folded imager. And while optical glass is generally suitable, newer, lighter materials offering increased manufacturability are preferred. More particularly, optical-grade polymers such as optical polycarbonates or olefin materials are good choices for constructing the individual lenses and/or prism.

Notably, the horizontal field of view (HFOV) might include a full angle 160° in a plane parallel to the image plane and a vertical field of view (VFOV) that includes a full angle of 90° in a plane normal to the image plane. For applications such as in vivo imaging, a low conjugate ratio is required to image objects that are positioned close to the imaging system. The imaging system shown in FIG. 1 has a conjugate ratio of approximately 5.5.

Figure 2:
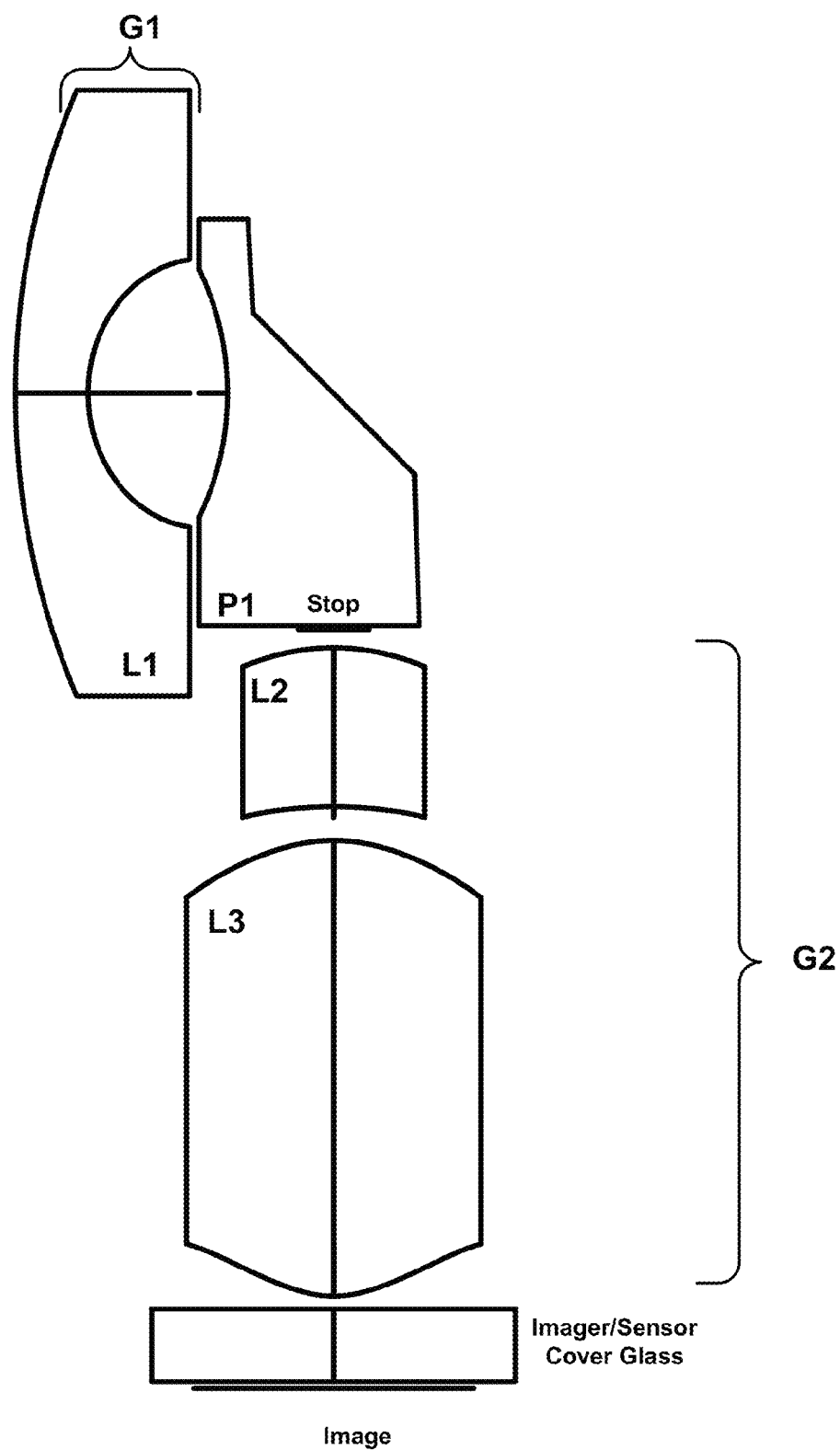
FIG. 2 shows a schematic of an alternative exemplary folded imager according to an aspect of the present disclosure.

With reference to FIG. 2, there is shown an exemplary alternative imaging system having a folded optical axis according to an aspect of this disclosure. As shown in that FIG. 2—and similarly to that shown in FIG. 1, this imaging system has a first lens group G1 having a negative refractive power, a prism P1 having a first surface that is concave P1S1 and a second surface that is reflective (mirror) P1S2, and a second lens group G2 having a positive refractive power.

As shown in FIG. 2, first lens group G1 comprises a single lens L1 having two refractive surfaces, convex surface L1S1 and concave surface L2S2 which exhibits an overall negative refractive power. The second lens group G2 is shown comprising only two lenses namely L2 and L3. Each of the lenses includes two refractive surfaces. The first lens in group G2, lens L2, has a convex refractive surface L2S1 and a concave refractive surface L2S2. The second lens in group G2, lens L3, has two convex refractive surfaces L3S1 and L3S2.

Figure 3:
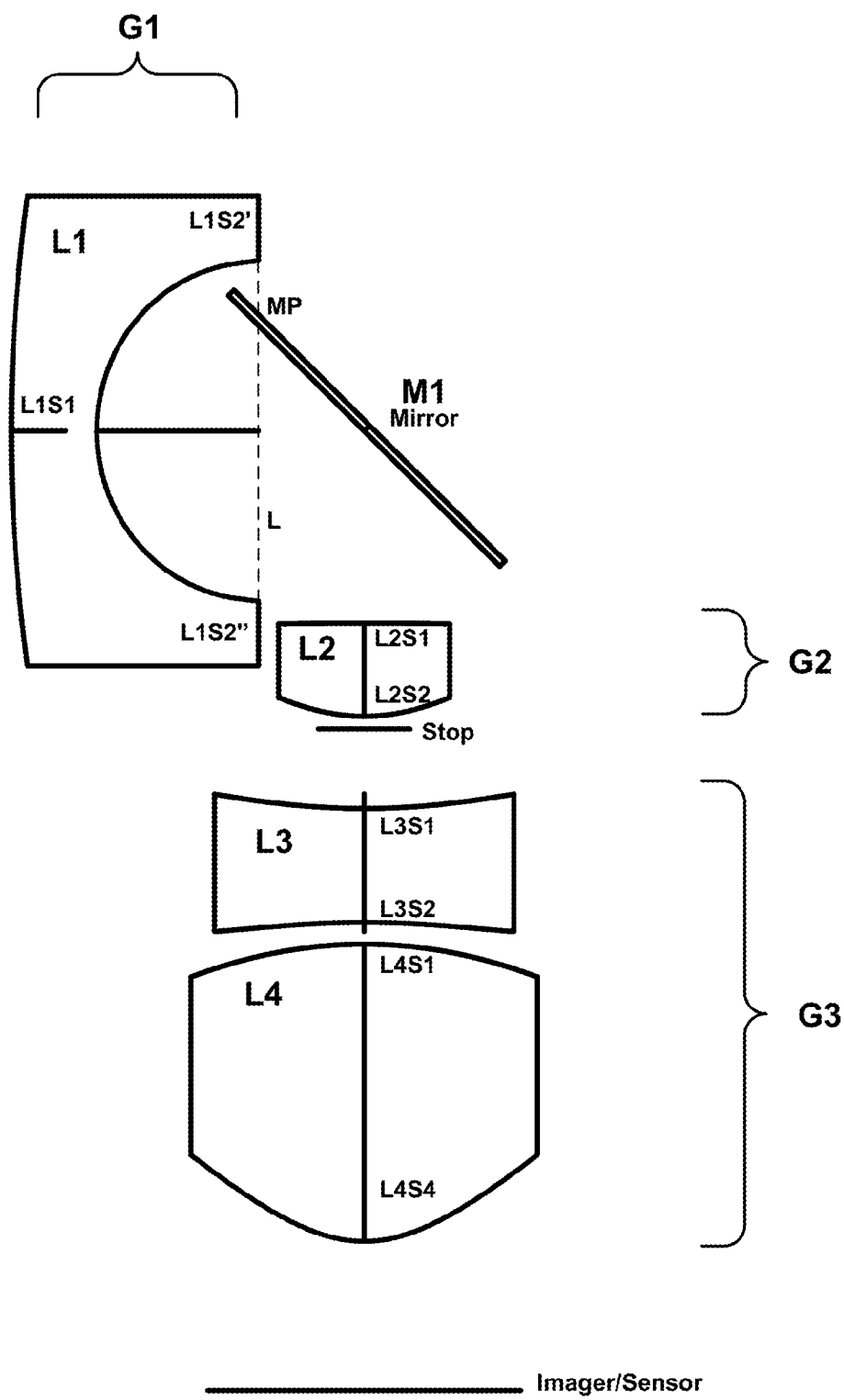
FIG. 3 shows a schematic of another alternative exemplary folded imager according to an aspect of the present disclosure.

Turning now to FIG. 3, there is shown another alternative embodiment of an imaging system having a folded optical axis according to an aspect of the present disclosure. As shown, this alternative imaging system has a first lens group G1 having a negative refractive power, a mirror M1, a second lens group G2 having a positive refractive power and a third lens group G3 having a positive refractive power.

As shown in FIG. 3, first lens group G1 comprises a single lens L1 having two refractive surfaces, convex surface L1S1 and concave surface L2S2 which exhibits an overall negative refractive power. The second lens group G2 is shown comprising only a single lens namely L2. Lens L2 has two refractive surfaces, a first substantially flat surface L2S1 and a second convex surface L2S2. An aperture or stop mechanism may be positioned at this second surface L2S2.

A third lens group G3 comprising two lenses L3 and L4 each having two refractive surfaces. More particularly, lens L3 has two concave surfaces L3S1, L3S2, while lens L4 has two convex surfaces L4S1 and L4S2.

With continued reference to FIG. 3, it is shown that the second surface of lens L1 has a pronounced concave surface L1S2. As shown, the mirror, M1, is positioned such that a portion of that mirror is within the concave region of that second surface L1S2. That is to say, if a line L were extended from the inner surfaces of that lens L1 from points L1S2' and L1S2" that line would intersect the mirror at some point MP.

Figure 4:
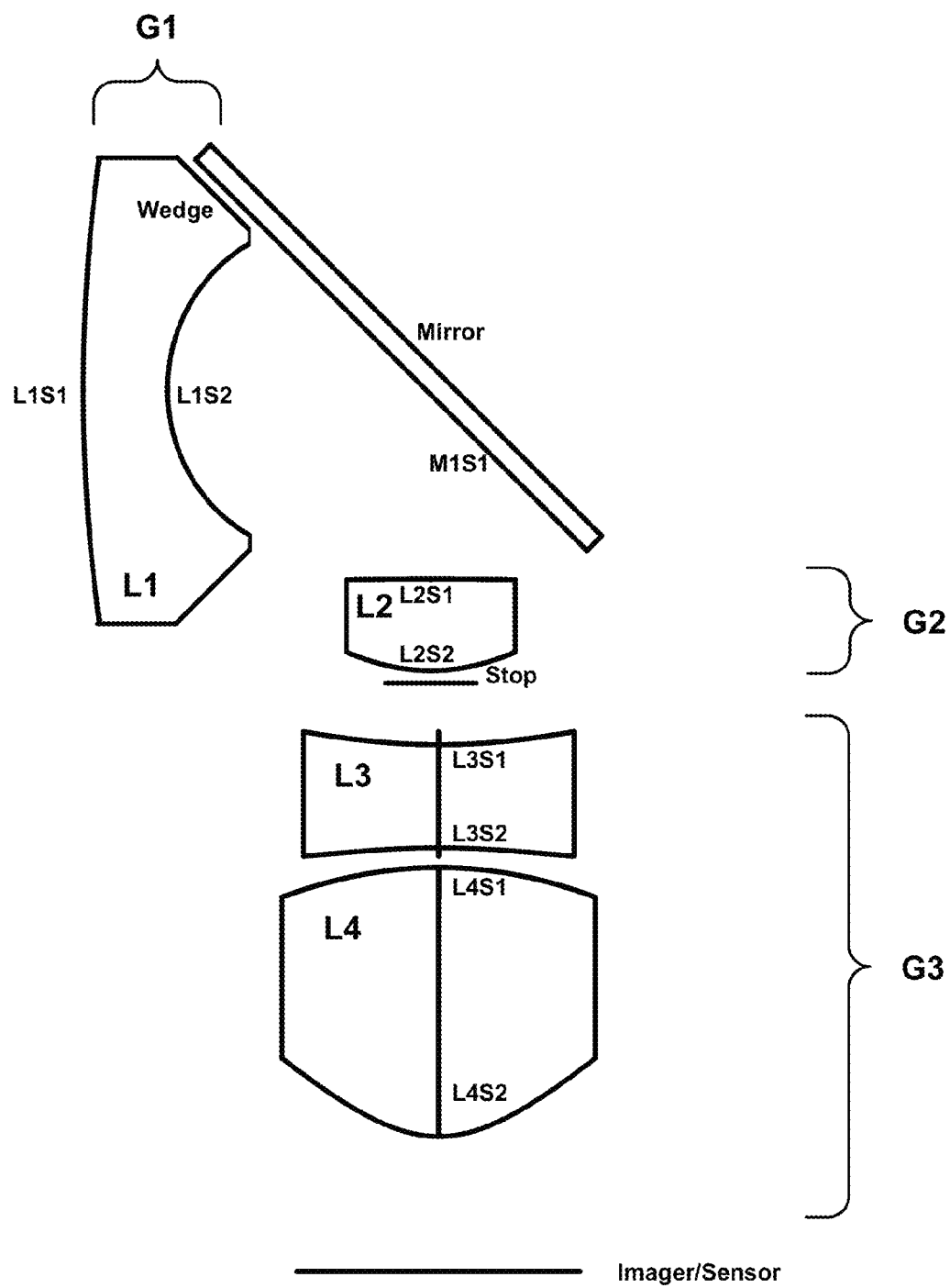
FIG. 4 shows a schematic of an alternative of the exemplary folded imager of FIG. 3.

FIG. 4 shows an alternative system to that shown in FIG. 3. In particular, the alternative imaging system comprises three lens groups namely, G1, G2 and G3, wherein G1 comprises a single lens L1, G2 comprises a single lens L2 and G3 comprises two lenses L3 and L4. All of the refractive surfaces of the lenses are substantially as those shown previously in FIG. 3.

Notably however, the top surface of lens L1 has been shaped such that a "wedge" shape is produced in that top surface. In this manner, mirror M1 may extend outside of the curved inner refractive surface L1S2 along that wedge surface. As a result, the mirror M1 may be positioned adjacent to the wedge surface to provide additional stability and alignment to these components.

Figure 5:
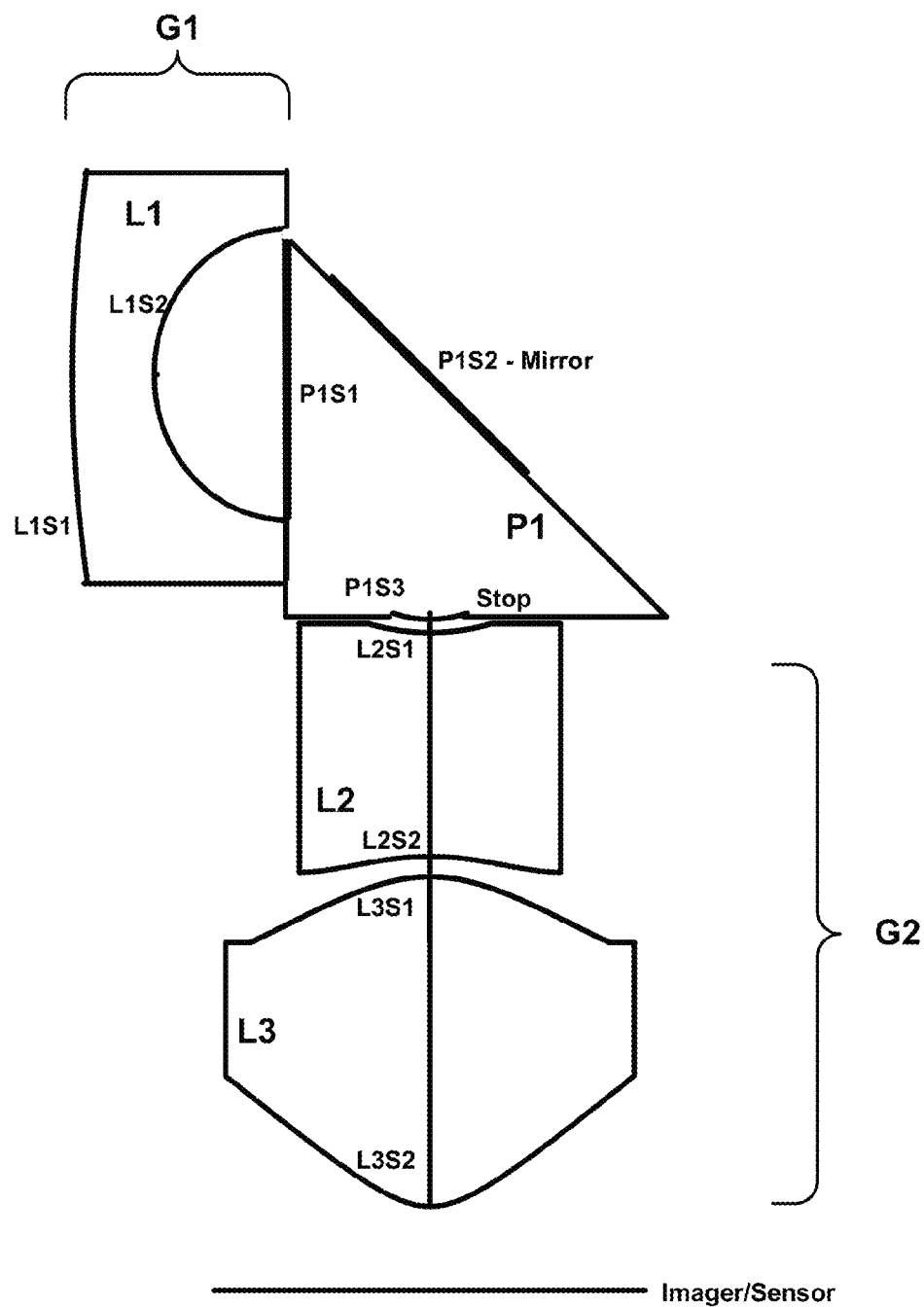
FIG. 5 shows a schematic of a folded imager according to an aspect of the present disclosure having a prism with convex surface.

Turning now to FIG. 5, there is shown yet another alternative embodiment of an imaging system according to an aspect of the present disclosure. As shown in that FIG. 5 the alternative imaging system has a first lens group G1 having a negative refractive power, a prism P1 having a first surface that is substantially flat P1S1, a second surface that is reflective (mirror) P1S2, and a third surface that is slightly convex P1S3, and a second lens group G2 having a positive refractive power.

The first lens group G1 comprises a single lens L1 having two refractive surfaces, convex surface L1S1 and concave surface L2S2, which exhibits an overall negative refractive power. The second lens group G2 is shown comprising only two lenses namely L2 and L3. Each of the lenses includes two refractive surfaces. The first lens in group G2, lens L2, has a concave refractive surface L2S1 and a second concave refractive surface L2S2. The second lens in group G2, lens L3, has two convex refractive surfaces L3S1 and L3S2.

Accordingly, light from an object will pass through L1 and enter prism P1 in which it is substantially reflected by mirrored surface P1S2. The reflected light is directed through convex surface P1S3 which may optionally include an aperture or other stop. The folded light is then directed through group G2, including lenses L2 and L3 which effect its formation of an image.

Figure 6:
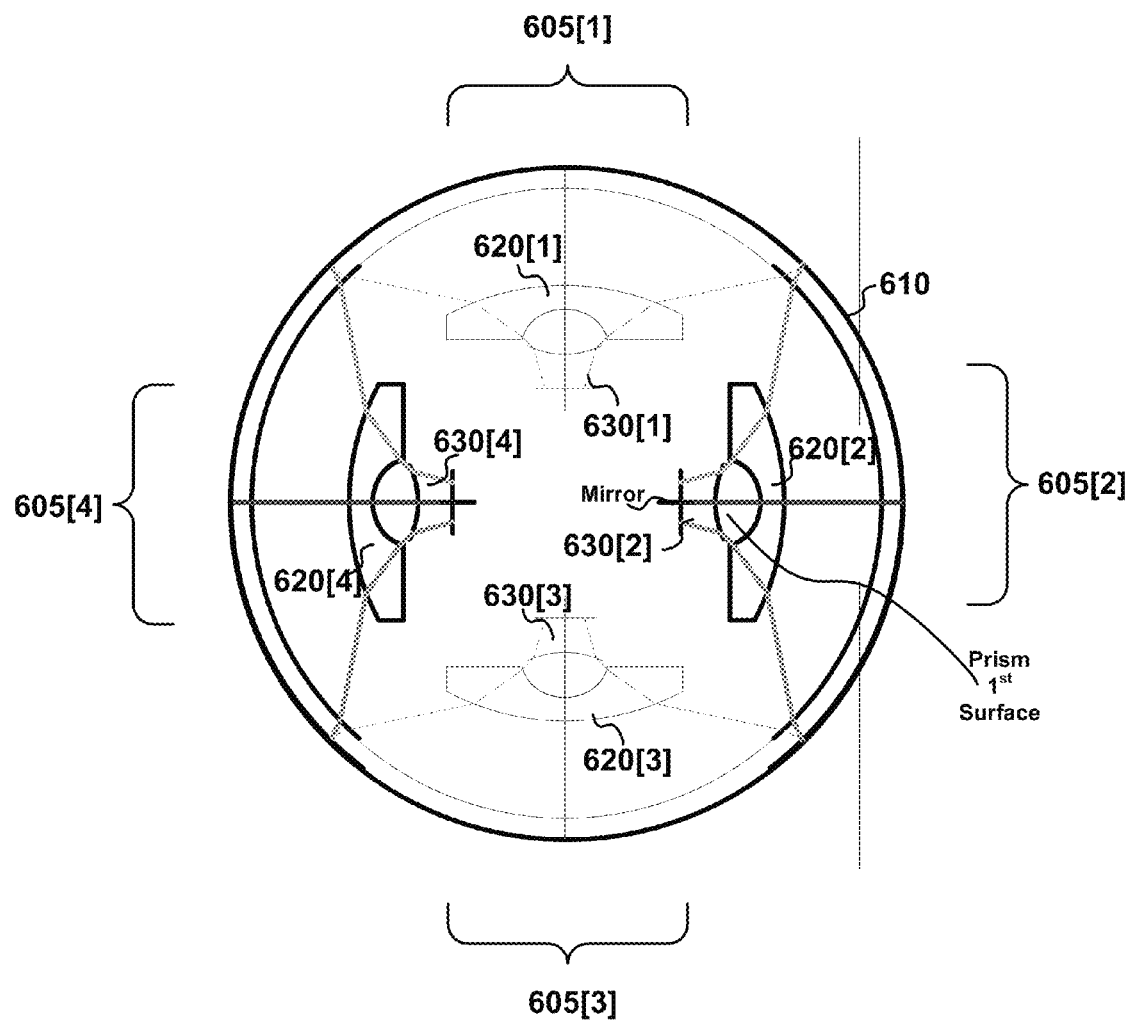
FIG. 6 shows in schematic form a top-cutaway-view of an exemplary panoramic imaging system employing four folded imagers according to an aspect of the present disclosure.

Turning now to FIG. 6, there is shown a top-cutaway view of an imaging system assembly according to an aspect of the present disclosure which advantageously permits imaging over a full 360 degree field-of-view.

The imaging system assembly 600 as shown in FIG. 6 may advantageously comprise a "capsule" imaging system, that is to say an imaging system that is positioned within and enclosed within a capsule shaped container. Advantageously, and according to yet another aspect of the present disclosure—such configuration may permit the imaging of the entire circumference of the capsule.

In a preferred embodiment, the capsule may be oblong in shape and the imaged circumference comprises the perimeter of a cross-section in a transverse plane normal to the longitudinal (longest) axis of the capsule. Advantageously, the capsule may have a substantially cylindrical mid-section with domed shaped ends, in which case the circumference is that of a circle. As may be appreciated, different application may require somewhat different shapes and the capsule need not be symmetrical about the longitudinal axis. For example, the capsule may have an elliptical rather than a circular circumference.

In the exemplary embodiment shown in FIG. 6, positioned within a capsule housing 610 (shown with top cut-away) are optical and other components which form an imaging system having a folded optical axis as shown and described previously. More particularly shown positioned within the capsule housing 610 are four component (folded) imagers, 605[1], 605[2], 605[3] and 605[4]. Each of the individual component imagers are positioned such that their horizontal (transverse) field of view (FOV) overlaps with the FOV of the adjacent imagers.

Accordingly, each of the individual imagers 605[1], 605[2], 605[3] and 605[4] has a FOV which is substantially greater than 90 degrees (FOV>>90) and as a result at least a full 360 degrees is imaged by the combined image(s). It should be noted, that while we have shown four (4) individual imagers within the capsule housing 610, those skilled in the art will appreciate that a greater or lesser number of imagers may be employed as practical and manufacturable.

As already noted, each of the individual imagers 605[1], 605[2], 605[3] and 605[4] are exemplary of those already described with respect to FIG. 1 and FIG. 2. More particularly, it is observed from this top view first lenses 620[1] . . . 620[4] which comprise Lens L1 of Group G1 in the earlier presented figures. Similarly, it may be seen from this view the top of prisms 630[1] . . . 630[4], which are depicted as prism P1 in the earlier presented figures. As can be appreciated by this arrangement, light from the full 360 degrees of the capsule circumference is captured by lenses 620[1] . . . 6207[4], and folded through the action of a respective prism 630[1] . . . 630[4], and subsequently imaged onto an appropriate sensor(s) positioned beneath (in this view) the lens/prism assembly positioned in the capsule.

Figure 7:
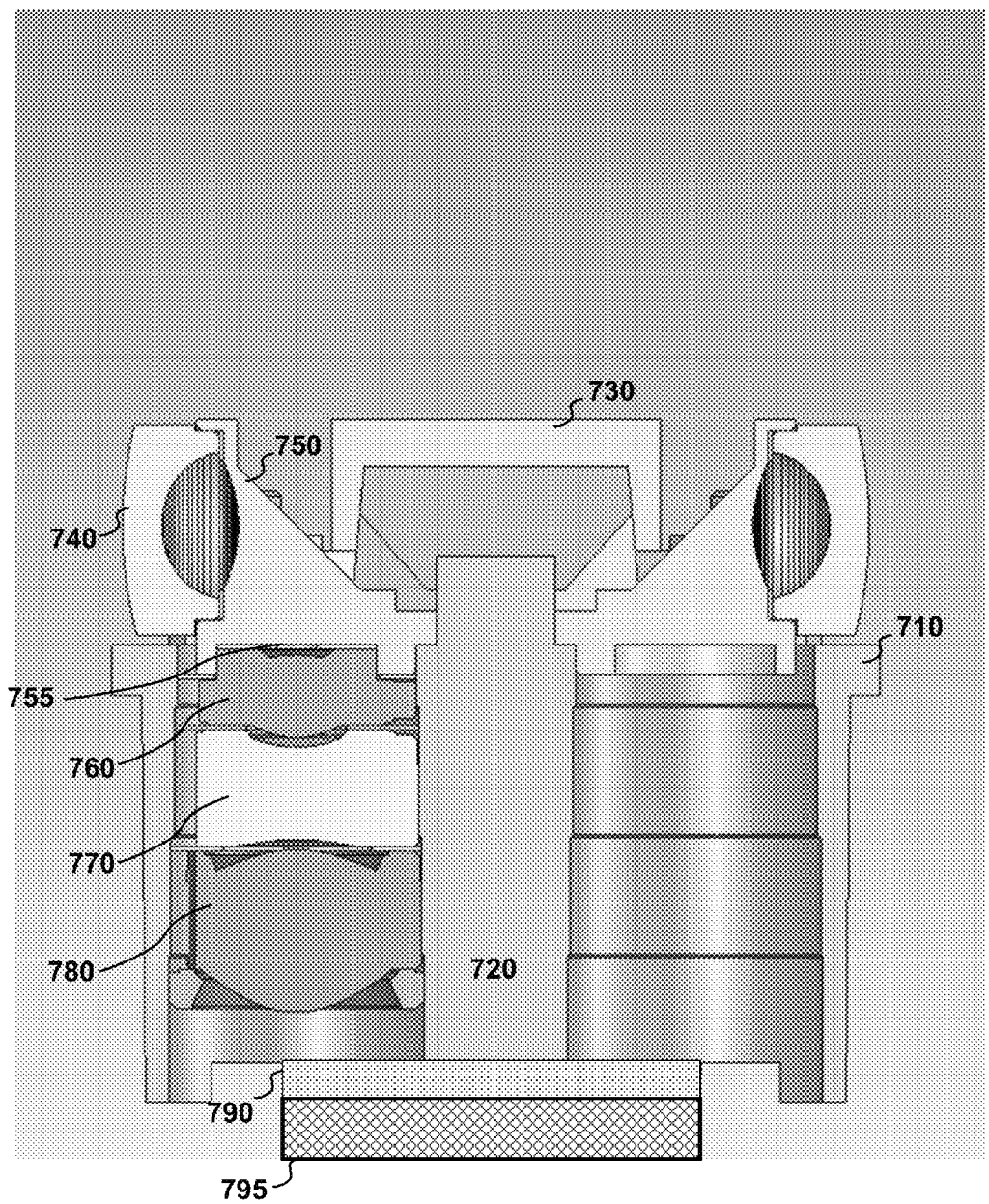
FIG. 7 shows in schematic form side-cutaway-view of an exemplary panoramic imaging system employing four folded imagers according to an aspect of the present disclosure.

With these structures in mind, we may now turn to FIG. 7, which shows a side-cutaway view of an assembled imaging system having a folded optical axis according to an aspect of the present disclosure. As can be readily appreciated by those skilled in the art, such an apparatus may be used in a capsule as appropriate.

Figure 11:
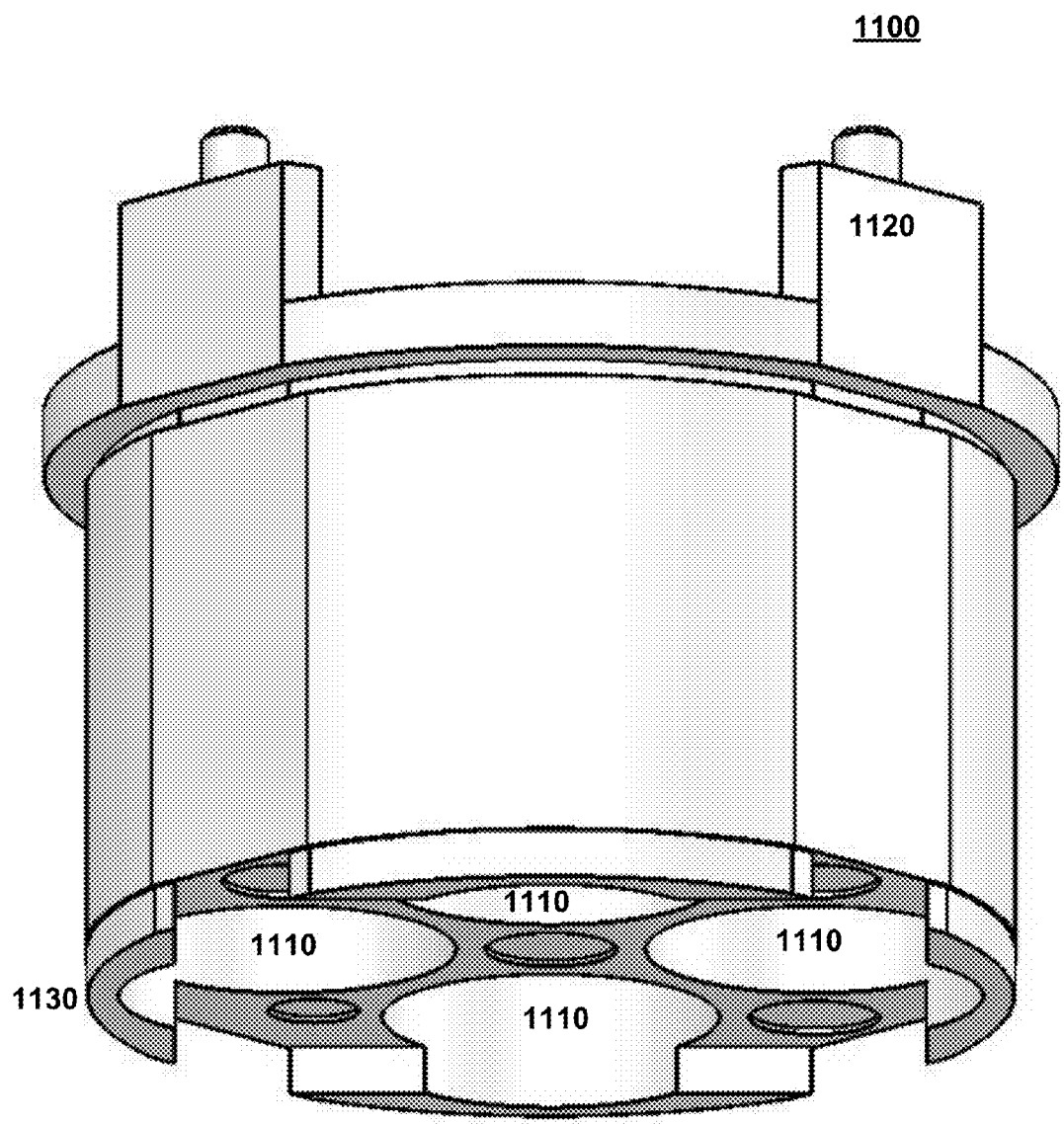
FIG. 11 shows in schematic a bottom-side perspective view of an exemplary lens barrel and bores according to an aspect of the present disclosure.
Figure 12:
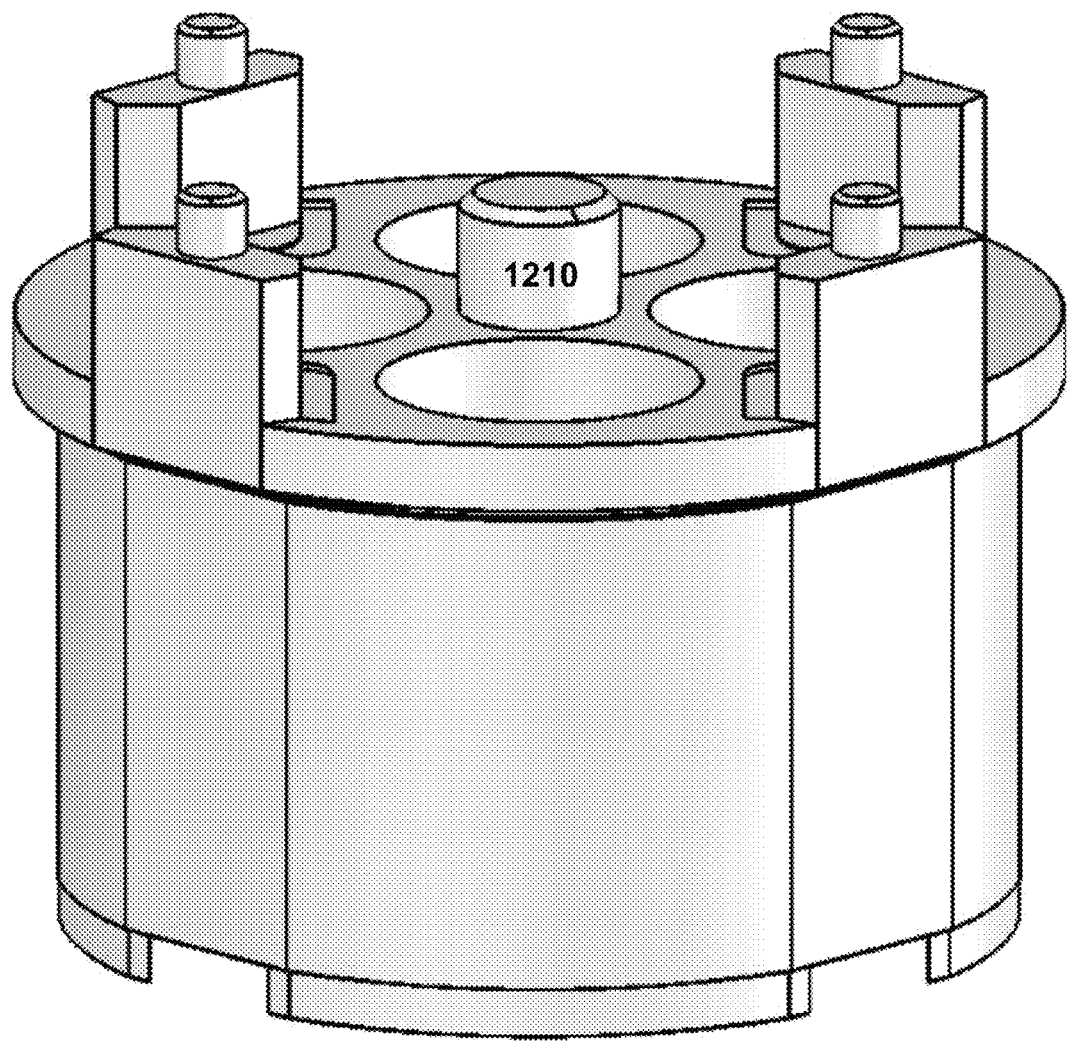
FIG. 12 shows in schematic a top-side perspective view of an exemplary lens barrel and bores according to an aspect of the present disclosure.

For easier understanding of some of the structure(s) shown in this FIG. 7, simultaneous reference to FIG. 11 and FIG. 12, which show a lens barrel from top-perspective and bottom-perspective views respectively, will be helpful to the reader.

Continuing with the discussion of FIG. 7, shown therein is a lens barrel 710 which in a preferred embodiment may be substantially cylindrical in overall shape. The particular configuration depicted in this FIG. 7 is of a lens barrel 710 having—for example—four cylindrical bores spaced apart by 90 degrees (See, e.g., FIG. 11—1110 [1] . . . 1110 [4]). The bores 1110 [1] . . . 111 [4] contain/align/isolate lens/optical assemblies. Two bores are shown in the cross section of FIG. 7, but the embodiment has a total of four bores. Moreover, for illustrative purposes, only one bore is shown populated with lens elements, but in practice all bores are populated. The lenses 760, 770, and 780 are substantially circular in shape, having diameters slightly smaller than the inner diameter of the bore, except for a flat on the side of each lens where a gate for injection molding is located. In FIG. 7 the flats are located on the left hand side of each lens, resulting in a gap between the lenses and the bore in cross section.

Depending upon the particular configuration, the barrel 710 may be open only at one end or alternatively may have a cover or cap placed at each end. Additionally, the lens barrel may have more or fewer bores as dictated by the application.

Positioned within each bore of the barrel 710—shown in a stacked arrangement—are (from an image side to an object side) a lens 780, a lens 770, a lens 760, a prism 750 which is part of a monolithic prism element comprising four prisms disposed at 90 degree angles from each other, and a lens 740. As can be understood with recollection to FIG. 1, the topmost lens in the figure, lens 740, comprises the first lens L1 in the first group G1, the prism 750 comprises the prism P1, while group G2 comprises lens L2 (760), lens L3 (770) and lens L3 (780).

In addition, a cover glass 790 is positioned beneath the second group G2 and disposed beneath the cover glass 790 is a sensor 795. In this manner, light from an object (not specifically shown) is collected through the effect of lens 740, folded through the effect of prism 750, and subsequently imaged onto a sensor 795 via cover glass 790. Of course, those skilled in the art will at this point recognize that a number of variations to this general structure are possible, most notably the number of lenses comprising the various lens groups and their refractive characteristics.

In particular, while we are showing the exemplary embodiments as having four (4) individual imagers with folded axes, those skilled in the art will appreciate that more or fewer may be used as applications dictate. As noted earlier, in a preferred embodiment each of the individual imagers captures or exhibits an enhanced field of view which is greater than 90 degrees. Accordingly, each individual field of view captured by an individual imager will overlap with its adjacent imagers. In this manner, a full, panoramic 360 degree image may be constructed from images captured by each individual imager. To capture such images, each of the individual imagers may be oriented substantially 90 degrees from one another when positioned within the barrel and bores shown in FIG. 7.

The imaging assembly shown in FIG. 7 may be advantageously assembled individually, or as a series of sub-assemblies, depending upon particular manufacturing method(s) employed. In particular, when individual components are employed, the assembly process may include positioning the individual elements within the bores of the barrel 710, positioning lens(es) 780, positioning lens(es) 770, positioning lens(es) 760, positioning prism(s) 750, and finally positioning lens(es) 740. The entire assembly may then be maintained in overall position by applying prism cover assembly which may secure the entire assembly into barrel 710.

In a preferred embodiment, lens 760 aligns to prism 750 via concentric features on each part. The bottom surface of the prism has an annular protrusion 755 and fits into the inner diameter of this annulus. Consequently, and advantageously, one possible assembly flow is: 1) Place 4 lenses 760 on prism with prism inverted. 2) Place barrel (inverted onto prism so that lenses 760 enter the bores of the barrel and bond prism to barrel. 3) Load lens 770. 4) load lens 780. 5) load retaining ring (not labeled) and bond ring to barrel. 6) Attach lenses 740. Lens 740 fits concentrically within a circular opening in the face of the prism.

In addition, apertures may be placed between each lens and between lens 760 and the prism and lens 740 and the prism during the assembly. These apertures may be annular rings stamped from a sheet of black plastic. Also, the bores in barrel 720 may be tapered to facilitate injection molding. In a preferred embodiment, the taper is from bottom to top so that successively smaller-diameter lens elements may be loaded from bottom to top. The taper could be in the opposite direction, in which case the lenses would be loaded in the opposite order. Moreover, a different (i.e., machined) bore might have no taper so that lenses could be loaded from either side.

The lens barrel 710 may include downwardly protruding legs that straddle/engage the sensor 795 and/or the cover glass 790. In a particular embodiment such as that contemplated with four independent imaging systems, the sensor 795 may have four distinct regions containing pixels that convert incident photons into signal electrons. The area outside these regions may advantageously contain non-photosensitive circuitry such as pixel readout, amplification, and chip I/O. A sensor package such as a chip-scale package may have outer envelope and cover glass accurately registered to the pixel regions, for example within +/−0.10 mm. The lens assembly may then be passively aligned so that each objective is approximately centered on a active pixel region by positioning the assembly onto the sensor so that the legs straddle the sensor and/or cover glass. Ideally, the clearance between the sensor and barrel legs is less than 0.1 mm.

Advantageously, and according to an aspect of the present disclosure, the back focal distance may be passively set by positioning the cover glass and lens barrel such that an image is focused onto the sensor with the lens assembly resting on the cover glass. As a result, no active focus adjustment is required.

Figure 8:
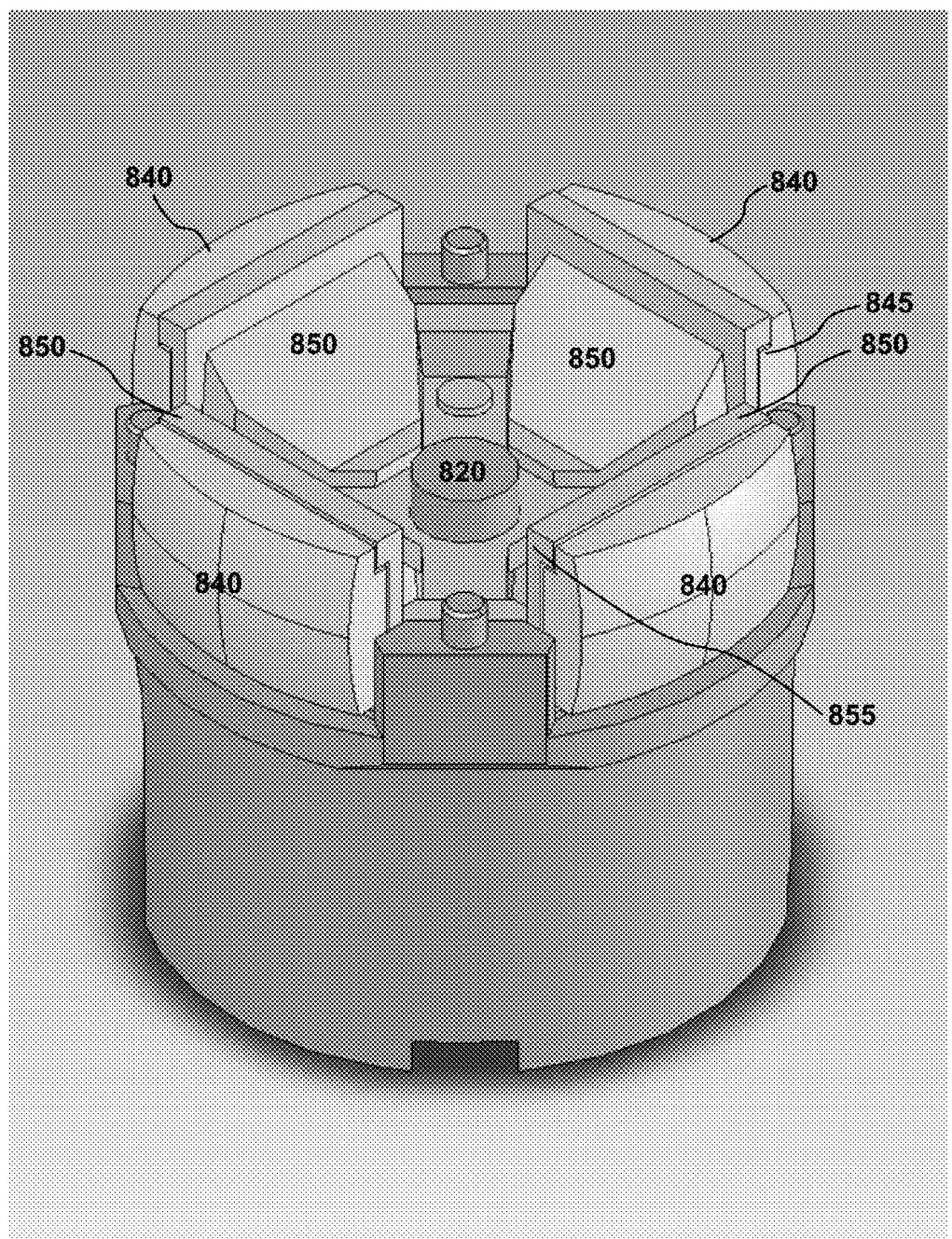
FIG. 8 shows in schematic form a perspective cutaway-view of an exemplary panoramic imaging system employing four folded imagers according to an aspect of the present disclosure.

Turning now to FIG. 8, there is shown a perspective view of a partially assembled panoramic imaging system employing four imagers having folded axis according to the present disclosure. In particular, it is shown that positioned within or as part of the lens barrel are boss 820, four prisms 850, and four lenses 840. Advantageously, the four prisms may be constructed of a single, monolithic part that may be formed—for example—by injection molding processes.

Further shown in this figure are notches or recesses 855 formed on a front face of each prism 850, and mating tabs 845 formed on back (prism side) of each lens 840. Such notches and tabs provide a secure, positive alignment between the lenses 840 and the prisms 850.

Figure 9:
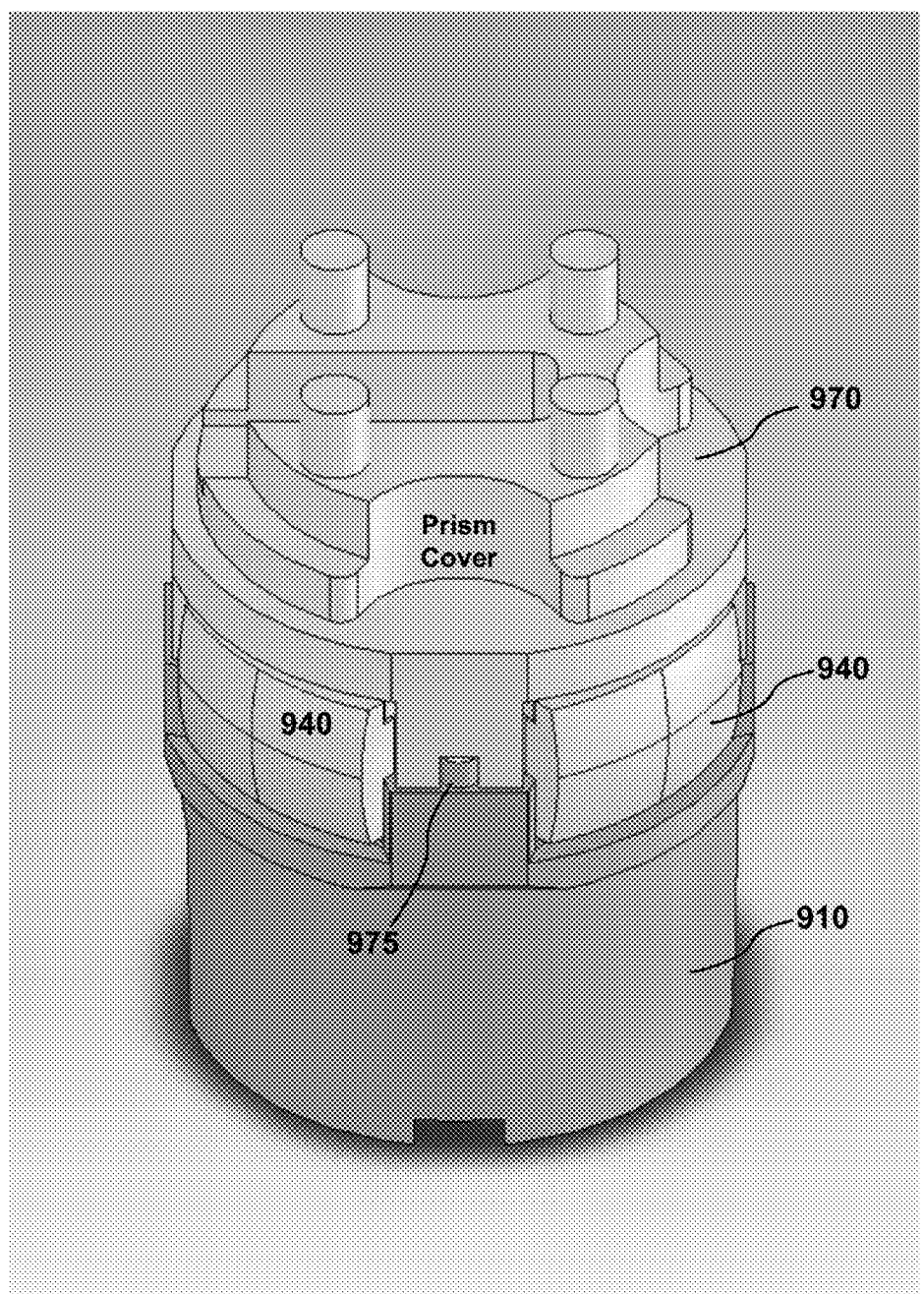
FIG. 9 shows in schematic form a perspective view of an assembled panoramic imaging system according to an aspect of the present disclosure.

FIG. 9 shows a perspective view of an assembled panoramic imaging system employing four imagers having folded optical axis according to the present disclosure. In particular, shown positioned on top of barrel 910 are lenses 940 wherein the entire assembly is "capped" by a prism cover 970. As shown in that figure, the prism cover 970 may be aligned and/or positioned through the use of locator pins 975 or tabs formed as part of the barrel 910. In addition, prism cover 970 may have fins (not specifically shown in this figure) that project into any voids or spaces between the prisms, thereby blocking stray light that would otherwise pass out the side of one prism into the side of another prism.

As those skilled in the art will readily appreciate—with optical apparatus such as the ones that are the subject of the present disclosure—stray light is any light that passes from an object through the optical system along an unintended path and impinges on the image plane. Unfortunately, stray light is sensed by the sensor but is not in fact a part of the actual object image. As a result, such stray light may adversely affect the quality of the actual image so sensed.

Fortunately, stray light may be reduced by reducing the reflectivity and/or transmissivity of any surfaces within the overall system assembly which are not intended to reflect or transmit light. The lens barrel may be formed of a black opaque material to reduce reflections from the sides of the bores and to prevent light from one objective passing through the barrel to another objective. As may be observed from FIGS. 11 and 12, the bore structures within the barrel serve to isolate light in one bore from leaking to another bore.

Additionally, prism surfaces that are not intended to reflect or pass light may be coated with an opaque and absorbing substance such as black paint or epoxy. Consequently, folded imagers constructed according to the present disclosure should not have a substantial amount of light leaking into an undesired optical path. Still further, folded imagers according to the present disclosure will produce images exhibiting minimal amounts of stray or undesired or unintended light from forming/affecting those images.

Figure 10:
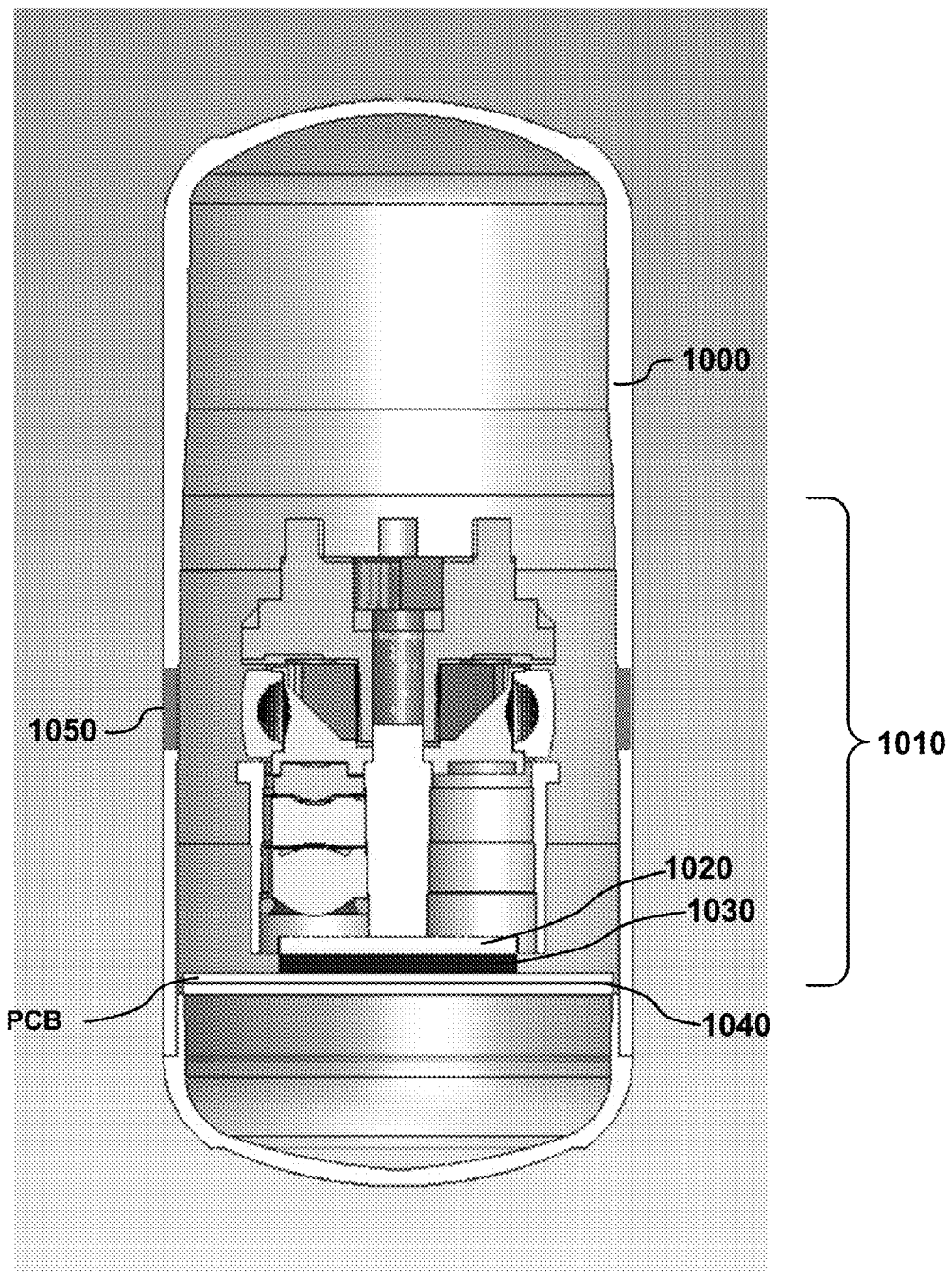
FIG. 10 shows a schematic of an exemplary capsule containing an assembled panoramic imaging system employing folded imagers according to an aspect of the present disclosure.

FIG. 10 shows a cutaway-side view of a panoramic capsule which contains a panoramic imaging system having a number of individual imagers with folded optical axis according to an aspect of the present disclosure. More particularly, capsule body 1000 may be made from any small, preferably swallowable, bio-compatible material. Along the sides of the capsule body 1000 are a window 1050 (or a number of windows), which is positioned in substantial alignment with panoramic camera assembly 1010 that is securely positioned within the capsule 1000. Light enters the capsule through a window, circumferential band 1050. The longitudinal length of the band may be between 3 and 6 mm, for example.

Positioned beneath the assembly 1010 is a cover glass 1020 which permits captured light to exit the assembly 1010 and impact the imaging sensor 1030. In this configuration, additional electronics and/or processing may be provided upon PCB 1040.

Accordingly, as the overall capsule 1000 moves through—for example, a large intenstine—light entering window 1050 is captured by lenses L1, folded by prism P1, and further directed to cover glass 1020 and sensor 1030 through the effect of lenses L2, L3, and L4. Since each one of the individual folded imagers captures images from a field of view that is greater than 90 degrees, the images from each of the individual imagers may be combined into an overall panoramic image. Accordingly, such a panoramic capsule may panoramically capture images from a trip through—for example—a large intestine. Once captured, the images may be transmitted wirelessly to a receiver located outside the capsule (and the intestine) or alternatively be off-loaded upon passing of the capsule.

Turning now to FIG. 11, there is shown a bottom-side perspective view of an exemplary lens barrel 1100 and bores 1110 according to an aspect of the present disclosure. As may be further observed from this perspective view are locator pins and tabs 1120 which may advantageously positively engage the prism assembly and prism cover (not shown). Also shown are a number of legs or projections 1130 which downwardly protrude from barrel structure which may serve to positively locate windows and sensor assemblies (not shown).

FIG. 12 is a top-side perspective view of the barrel shown in FIG. 11. Shown in this figure—in addition to those elements shown in FIG. 11, is a "boss" 1210 which is shown located substantially in the center of the bores, and advantageously serves to locate the prism assembly (not shown).

Figure 13:
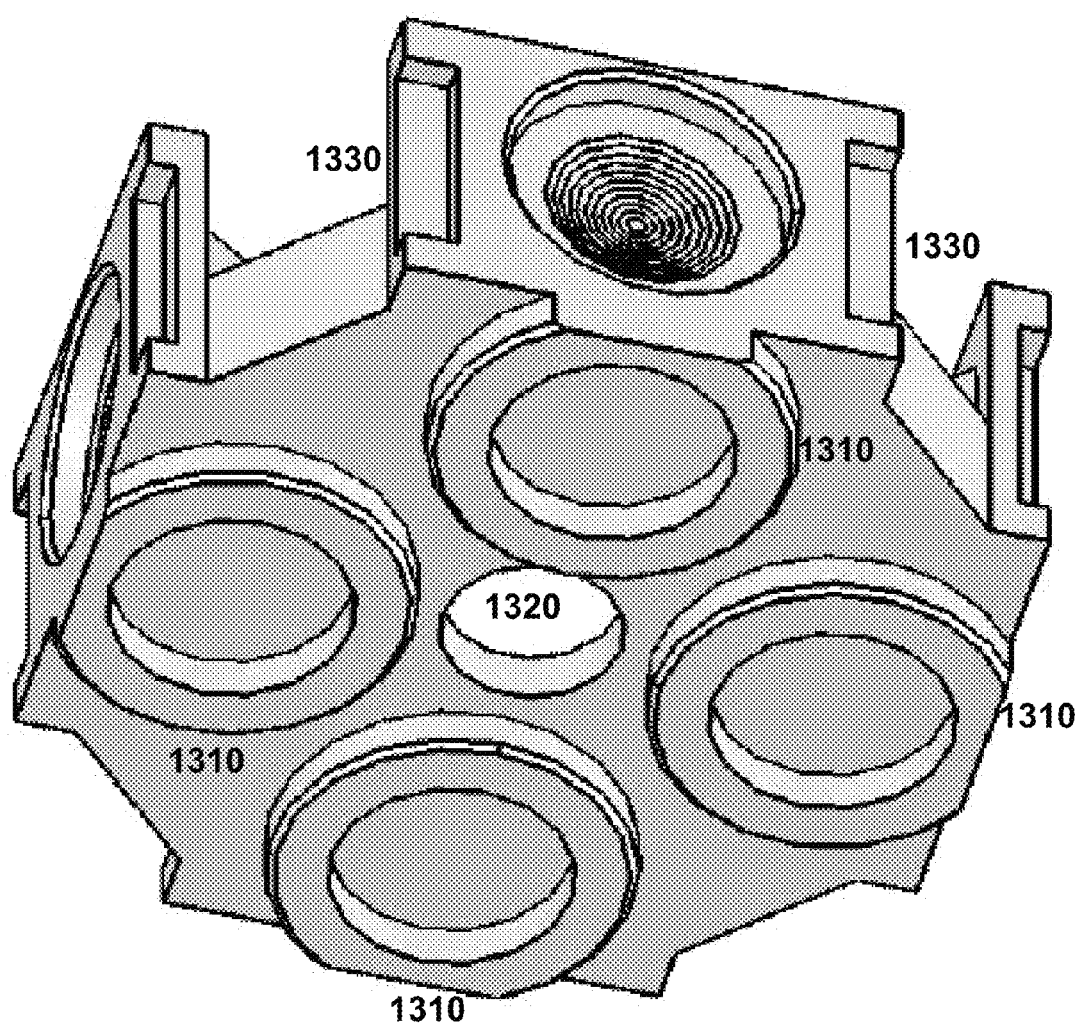
FIG. 13 shows in schematic a bottom perspective view of an exemplary prism assembly according to an aspect of the present disclosure.
Figure 14:
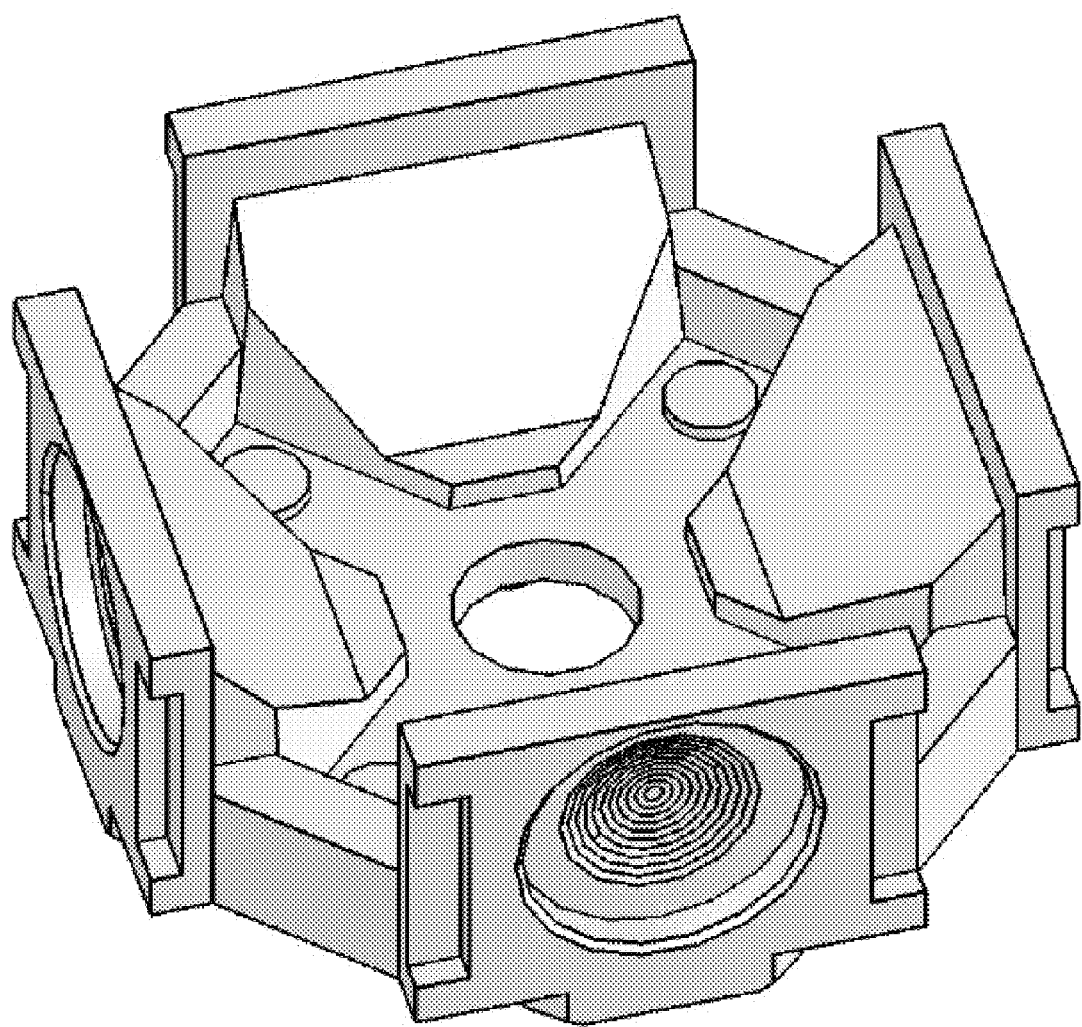
FIG. 14 shows in schematic a top perspective view of an exemplary prism assembly according to an aspect of the present disclosure.

FIG. 13 is a bottom perspective view of the prism assembly according to an aspect of the present disclosure. As shown therein and noted previously, such an "assembly" may comprise a single part or may be a number of parts assembled together. As shown in that FIG. 13 are annular protrusions 1310 which may advantageously fit within the bores of the barrel assembly (not shown). Advantageously, in addition to properly aligning the prism(s) with their respective bore, the annular protrusions serve to ensure that no stray light enters/ exits a particular prism/bore. Also shown is a locator hole 1320 into which may insert the boss shown previously. Finally, the recesses 1330 adjacent to prism face(s) serve to align additional lenses (not shown). FIG. 14 is a top perspective view of the prism assembly shown in FIG. 13. From this figure, it may be observed the substantially 90 degree relationship for each individual prism relative to one another.

Figure 15:
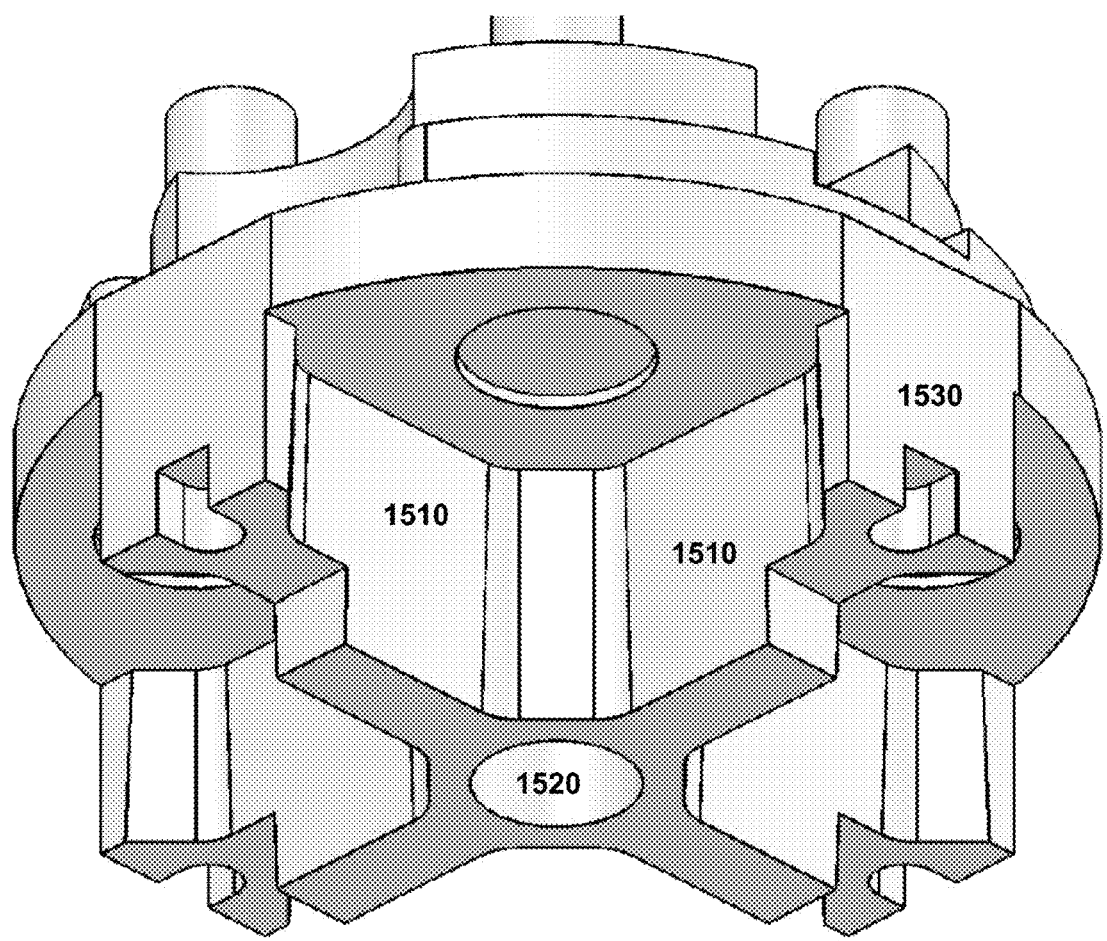
FIG. 15 is a schematic of a prism cover according to an aspect of the present disclosure.

FIG. 15 is a bottom perspective view of a prism cover 1500. As shown in this FIG. 15 are the skirts or fins 1510 which serve to optically isolate each of the individual prisms from one another. As may be appreciated, locator hole 1520 receives the boss (not shown) and individual locator tabs and recesses 1530 engage mated surfaces on the barrel (not shown).

Figure 16:
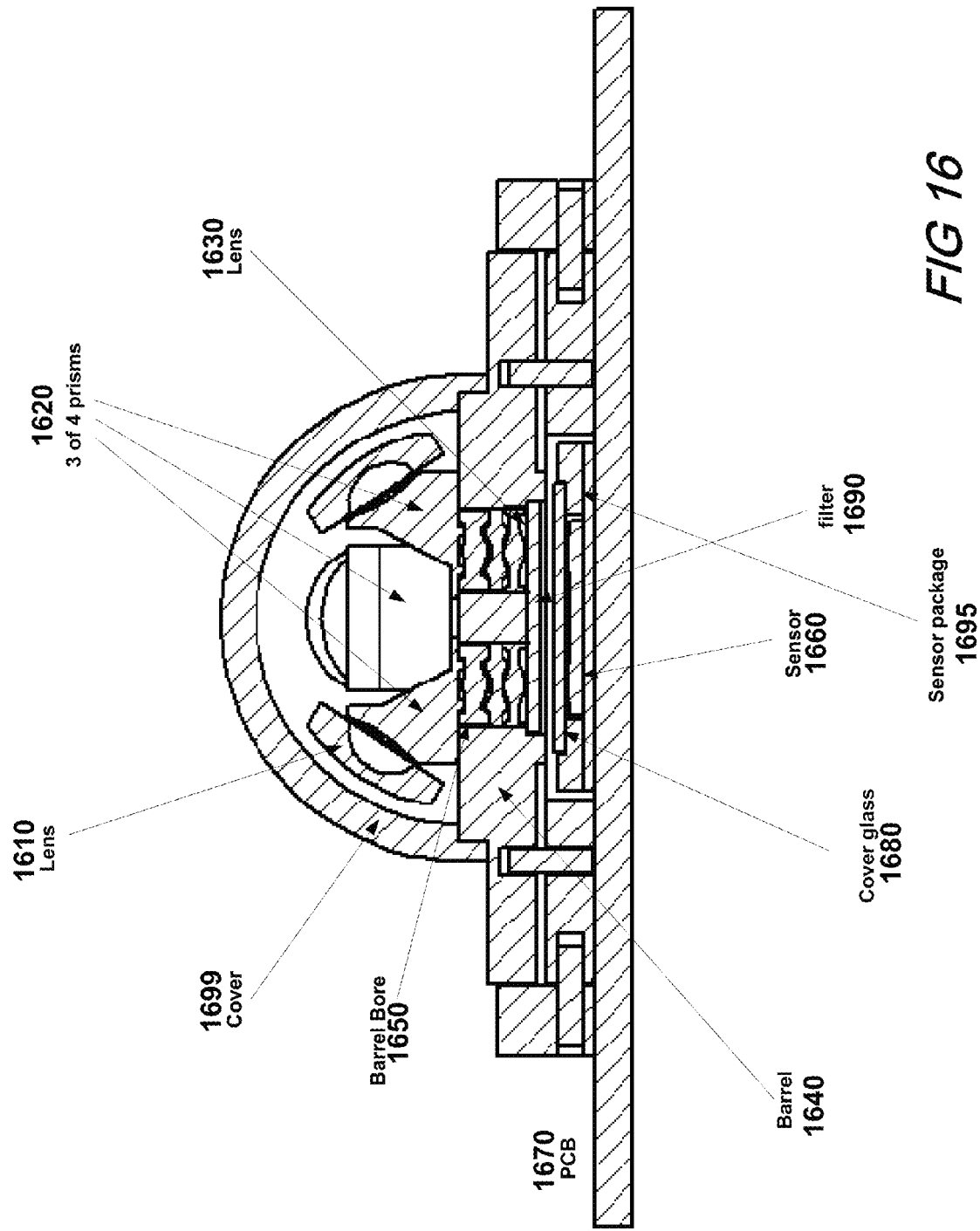
FIG. 16 is a schematic of an alternative embodiment of an imaging system having a folded optical axis according to an aspect of the present disclosure as may be used in a surveillance application.

FIG. 16 is a side cut-away view of an alternative embodiment of an imaging system having a folded optical axis as now taught and described. More particularly, the alternative embodiment may be used—for example—as part of a ceiling, wall, floor, table or other surface-mounted surveillance system.

With reference to that FIG. 16, shown therein is an imaging system comprising a number of lens(es) 1610 which collect light from an object(s) and directs that light into a corresponding prism 1620 having a concave surface. The prism redirects or "folds" the light through an angle of 60° into one or more other lenses 1630 positioned within bores 1650 of a barrel assembly 1640 which in turn direct the light onto the surface of a sensor 1660. For the example shown in which four separate images are formed onto the surface of the single sensor 1660, these separate images may be combined into a single panoramic image or displayed individually as an application requires. For a configuration in which each of the separate folded imagers exhibit a horizontal field of view of at least 90 degrees, the imaging system will image over a full 360 degree panorama.

Shown further in FIG. 16 are a PCB 1670 onto which the system may be positioned, and a cover glass 1680 and filters 1690 interposed between the sensor 1660 and lenses 1630 positioned within the barrel bores 1650. A cover 1699 is shown overlying the lenses/prisms assembly. As may be appreciated, such a cover may be made receptive to incoming light, but appear reflective so as to hide or conceal the inner workings of the structure. In addition, the cover may be transparent to received light in those regions necessary for reception by the lenses, etc., and not transparent in other regions. And while the shape of the cover is shown to be that of a "bubble"—those skilled in the art will readily appreciate that such shapes are also variable and dictated by the specific application requirements.

Additionally, the sensor 1660 may be packaged as a sensor package 1695 along with any filter(s) 1690 and or cover glass 1680 to facilitate its assembly.

At this point it is worth noting that images produced according to the present disclosure may advantageously be displayed in a side-by-side or other manner and do not necessarily need to be stitched together as may be common with "conventional" panoramic prints or displays. In this regard, each of the individual images would have portions of a scene shown in each individual image that overlaps other (adjacent) individual images. Alternatively, such images may be displayed in multiple rows thereby reducing the aspect ratio. For example, a first two images may be may be on a first display row while a second two images may be on a second display row. Generally, images produced according to the present disclosure may be displayed on the same medium at the same time without any limitation or restriction on orientation or position, and, for the purposes of this disclosure, said collection of images is a panoramic image.

As may be appreciated, more folded imagers (i.e., >4) or fewer folded imagers (i.e., <4) may be employed in such systems as applications dictate. For example, a ceiling mounted system may employ a full 360 degrees of coverage while a wall mounted system may only require 270 degrees of coverage. Notwithstanding these configuration options—and as may be readily appreciated—the folded imagers offer a designer a very compact configuration while providing substantial field of view(s).

Finally, at this point we note that an interesting "super conic" solution proposed by Alan Greynolds of Breault Research Organization expands in powers of the distance from a vertex to a point on a surface. The expansion may be described in terms of $s^2 = x^2 + y^2 + z^2$.

Starting with the conic equation for a surface, $kz^2 - 2Rz + x^2 + y^2 + z^2 = 0$, where k is the conic constant and R is the radius of curvature, a general power series expansion may be made of the form $Az^2 - 2Bz + C = 0$ and the constants are defined as: $A = k/R'$, $B = 1 + U_1 s^2 + U_2 s^4 + \ldots$, and $C = s^2/R + V_1 s^4 + V_2 s^6 + \ldots$.

Table 1 and Table 2 show the dimensional and overall characteristics of the optical elements by surface for the exemplary embodiment(s) shown and described herein.

TABLE 1

| Surface | Type | Comment | Curvature | Radius | Thickness |
|---|---|---|---|---|---|
| 1 | TOROIDAL | Window | 0.17699 | 5.65000 | 0.35000 |
| 2 | TOROIDAL | | 0.18868 | 5.30000 | 1.65000 |
| 3 | STANDARD | 1$^{st}$ Lens | 0.23604 | 4.23651 | 0.40000 |
| 4 | STANDARD | | 1.17566 | 0.85058 | 0.76600 |
| 5 | STANDARD | Prism 1$^{st}$ Surface | −0.74251 | −1.34677 | 0.58400 |
| 7 | STANDARD | Fold Mirror | 0.00000 | Inf | 0.00000 |
| 9 | STANDARD | Prism | 0.00000 | Inf | 0.00000 |
| 10 | STANDARD | | 0.00000 | Inf | −0.10000 |
| 11 | STANDARD | 2$^{nd}$ Lens | −0.76649 | −1.30465 | −0.83088 |
| 12 | STANDARD | | 1.27987 | 0.78133 | −0.09347 |
| 13 | STANDARD | 3$^{rd}$ Lens | 0.84388 | 1.18500 | −0.92685 |
| 14 | SUPERCONIC | | −0.51880 | −1.92753 | −0.10000 |
| 15 | SUPERCONIC | 4$^{th}$ Lens | −0.83339 | −1.19992 | −1.63563 |
| 16 | SUPERCONIC | | 1.15720 | 0.86464 | −0.50000 |
| 18 | STANDARD | Cover Glass | 0.00000 | Inf | −0.40500 |
| 19 | STANDARD | Image | 0.00000 | Inf | 0.00000 |

TABLE 2

| | Refractive | | | Superconic aspheric terms | | | |
|---|---|---|---|---|---|---|---|
| Surface | Index | Abbe number | Conic | U1 | V1 | U2 | V2 |
| 1 | 1.5855 | 29.91 | 0.00 | | | | |
| 2 | | | 0.00 | | | | |
| 3 | 1.5253 | 55.95s | 0.00 | | | | |
| 4 | | | 0.35 | | | | |

TABLE 2-continued

| Surface | Refractive | | Conic | Superconic aspheric terms | | | |
| --- | --- | --- | --- | --- | --- | --- | --- |
| | Index | Abbe number | | U1 | V1 | U2 | V2 |
| 5 | 1.5253 | 55.95 | −1.45 | | | | |
| 7 | | | 0.00 | | | | |
| 9 | 1.5253 | 55.95 | 0.00 | | | | |
| 10 | | | 0.00 | | | | |
| 11 | 1.5253 | 55.95 | −4.19 | | | | |
| 12 | | | −1.15 | | | | |
| 13 | 1.5855 | 29.91 | 0.92 | | | | |
| 14 | | | −15.00 | 1.7661 | −.8681 | −.4330 | 0.9628 |
| 15 | 1.5253 | 55.95 | −9.04 | −1.431 | 0.5129 | | |
| 16 | | | −2.92 | 0.9462 | 1.2851 | 0.4712 | −.0185 |
| 18 | 1.5168 | 64.17 | 0.00 | | | | |
| 19 | | | 0.00 | | | | |

At this point, while we have discussed and described our disclosure using some specific examples, those skilled in the art will recognize that my teachings are not so limited. Accordingly, our disclosure should be only limited by the scope of the claims attached hereto.

What is claimed is:

1. A capsule imaging system comprising:
a swallowable housing constructed from a bio-compatible material, said swallowable housing including one or more windows positioned in alignment with a plurality of folded imagers, said windows arranged as a circumferential band and having a longitudinal length of between 3 and 6 mm such that light entering the capsule via the one or more windows is received by at least one of the folded imagers, said swallowable housing containing:
the plurality of folded imagers, each individual folded imager exhibiting a horizontal field of view greater than 90 degrees such that the full circumference of the housing is simultaneously imaged, said plurality of folded imagers including:
a first lens group consisting of a single lens;
a second lens group;
a prism interposed between the first lens group and the second lens group for directing light exiting from the first lens group into the second lens group, said prism having a surface that is concave; and
a sensor that detects images simultaneously directed thereupon by the second lens group of each individual folded imager, said images subsequently combined into an overall panoramic image of internal structures of a body when swallowed.

2. The imaging system of claim 1 wherein each one of said folded imagers produces a respective image upon the sensor and the images so produced are combined into an overall image.

3. The imaging system of claim 2 wherein said overall image is a panoramic image.

4. The imaging system of claim 3 wherein said concave surface is that surface of the prism which receives light exiting the first lens group.

5. The imaging system of claim 1 further comprising:
a planar printed circuit board onto which is positioned the sensor and a cover enclosing the folded imagers and sensor.

6. A capsule imaging system having a folded optical axis comprising:
a swallowable housing constructed from a bio-compatible material, said swallowable housing including one or more windows positioned in alignment with a plurality of folded imagers, said windows arranged as a circumferential band and having a longitudinal length of between 3 and 6 mm, such that light entering the capsule via the one or more windows is received by at least one of the folded imagers;
a lens barrel positioned within said housing such that it is in axial alignment with the housing, said lens barrel including a plurality of boreholes formed therein, said boreholes being in axial alignment with said lens barrel and said housing;
the plurality of folded imagers positioned within the housing, a respective one for each borehole, each one having a horizontal field of view greater than 90 degrees, each one of said plurality of folded imagers including:
a single first lens for receiving light from one or more objects;
a prism for receiving light from said first lens and changing the direction of the received light such that it is redirected into its respective borehole; and
a second lens, positioned within the respective borehole, for receiving light from said prism; and
a sensor positioned within the housing and underlying the lens barrel, said sensor sensing light simultaneously from each second lens, said light forming images which are then combined into an overall panoramic image of internal structures of a body when swallowed.

7. The imaging system of claim 6 wherein each one of said folded imagers are optically isolated from one another.

8. The imaging system of claim 6 further comprising a prism cover positioned adjacent to said prisms.

9. The imaging system of claim 6 wherein the plurality of prisms are molded as part of a single molding.

10. The imaging system of claim 6 wherein said light sensed by the sensor are component images that are combined into an overall panoramic image indicative of a full 360 degree view relative to the housing circumference.

11. The imaging system 9 wherein said prism cover includes a number of isolators for optically isolating each one of said prisms from one another.

12. The imaging system 6 wherein said prism has a concave surface for receiving light from the first lens.

13. The imaging system of claim 6 wherein said prism changes the direction of the received light by 90 degrees.

14. The imaging system of claim 6 wherein said barrel includes a plurality of projections that straddle the sensor and axially align the sensor to the barrel.

15. The imaging system of claim 1 wherein each one of the plurality of prisms include features that mechanically align an adjacent lens with the prism.

16. The imaging system of claim 15 wherein the mechanical alignment features of the prism correspond to concentric features of the adjacent lens.

17. The imaging system of claim 15 wherein the mechanical alignment features of the prism comprise notches formed on a face of the prism that engage mating tabs formed on the adjacent lens.

18. The imaging system of claim 1 wherein the plurality of prisms are configured as a monolithic prism element comprising the plurality of prisms spaced apart from one another and that each individual one of the plurality of prisms is fixed in optical alignment with its respective first lens group and second lens group.

19. The imaging system of claim 1 wherein the imaged circumference of the housing comprises the perimeter of a cross-section in a transverse plane normal to the longitudinal (longest) axis of the system.

20. The imaging system of claim 6 wherein each one of the plurality of prisms include features that mechanically align an adjacent lens with the prism.

21. The imaging system of claim 18 wherein the mechanical alignment features of the prism correspond to concentric features of the adjacent lens.

22. The imaging system of claim 21 wherein the mechanical alignment features of the prism comprise notches formed on a face of the prism that engage mating tabs formed on the adjacent lens.

23. The imaging system of claim 6 wherein the plurality of prisms are configured as a monolithic prism element comprising the plurality of prisms spaced apart from one another and that each individual one of the plurality of prisms is fixed in optical alignment with its respective first lens group and second lens group.

* * * * *